United States Patent
Rooney

Patent Number: 4,866,068
Date of Patent: Sep. 12, 1989

[54] NOVEL HMG-COA REDUCTASE INHIBITORS

[75] Inventor: Clarence S. Rooney, Worcester, Pa.

[73] Assignee: Merck & Co., Inc., Rahway, N.J.

[21] Appl. No.: 150,585

[22] Filed: Feb. 1, 1988

[51] Int. Cl.[4] ..................... A61K 31/44; A61K 31/38; C07D 405/08; C07D 277/62

[52] U.S. Cl. ..................... 514/277; 514/367; 546/268; 548/165; 548/166; 548/178; 548/180; 549/292

[58] Field of Search .................. 546/268; 549/292; 514/277, 367; 548/165, 166, 178, 180

[56] References Cited

FOREIGN PATENT DOCUMENTS 0245003 11/1987 European Pat. Off. ............ 549/292

*Primary Examiner*—Glennon H. Hollrah
*Assistant Examiner*—Susan P. Treanor
*Attorney, Agent, or Firm*—Melvin Winokur; Joseph F. DiPrima

[57] ABSTRACT

Novel HMG-CoA reductase inhibitors of formulae (I) and (II) are disclosed:

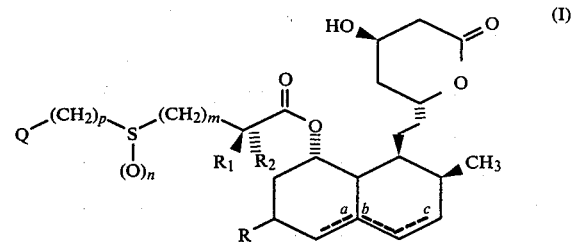

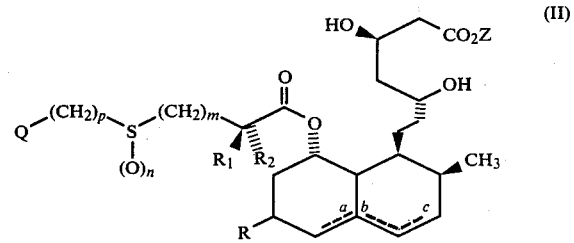

15 Claims, No Drawings

NOVEL HMG-COA REDUCTASE INHIBITORS

BACKGROUND OF THE INVENTION

Hypercholesterolemia is known to be one of the prime risk factors of ischemic cardiovascular disease, such as arteriosclerosis. Bile acid sequestrants have been used to treat this condition; they seem to be moderately effective but they must be consumed in large quantities, i.e. several grams at a time and they are not very palatable.

Mevacor® (lovastatin), now commercially available, is one of a group of very active antihypercholesterolemic agents that function by limiting cholesterol biosynthesis by inhibiting the enzyme, HMG-CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

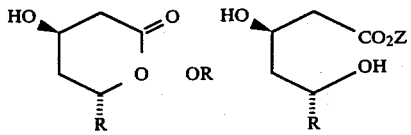

wherein: Z is hydrogen, $C_{1-5}$ alkyl or $C_{1-5}$ alkyl substituted with a member of the group consisting of phenyl, dimethylamino, or acetylamino; and R is:

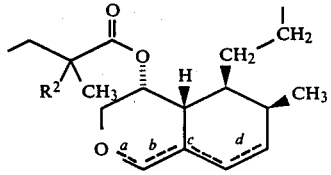

wherein Q is

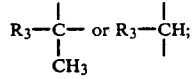

$R_3$ is H or OH; and $R^2$ is hydrogen or methyl; and a, b, c, and d represent optional double bonds, especially where b and d represent double bonds or a, b, c, and d are all single bonds, provided that when a is a double bond,

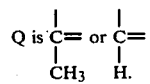

Japanese unexamined patent application J59-122,483-A describes antihypercholesterolemic compounds represented by the above general formula wherein R is

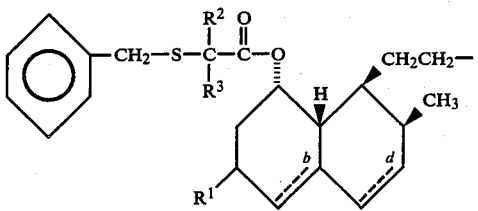

$R^1$ is methyl or hydrogen, $R^2$ is hydrogen, halogen or lower alkyl, $R^3$ is hydrogen, halogen or haloalkyl, and b and d represent optional double bonds.

Copending U.S. patent application Ser. No. 859,513 filed May 5, 1986 describes compounds of the above formula wherein R is

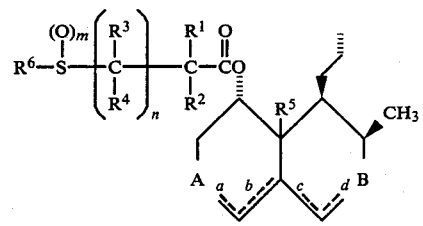

wherein $R^6$ is phenyl or substituted phenyl.

Copending U.S. patent application Ser. No 859,530 filed May 5, 1986 discloses compounds of the above formula wherein R is:

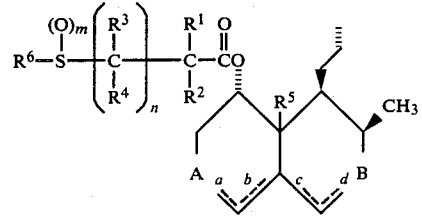

wherein $R^6$ is hydrogen or $C_{1-5}$alkyl.

DETAILED DESCRIPTION OF THE INVENTION

The specific HMG-CoA reductase inhibitors of the present invention are the compounds represented by the following structural formulae (I) and (II):

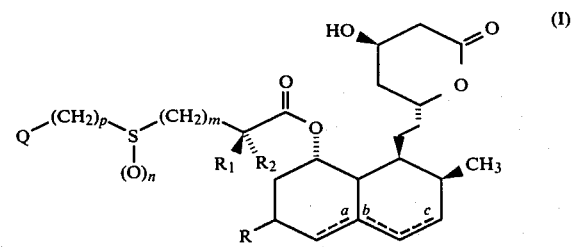

(I)

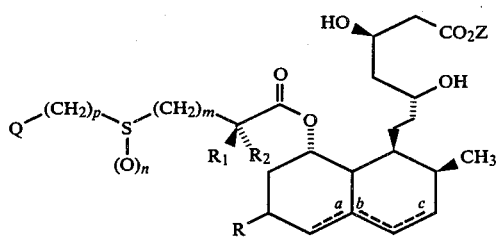

wherein:

Q is

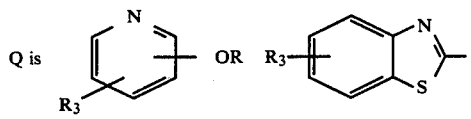

$R_1$ and $R_2$ are independently hydrogen or $C_{1-3}$alkyl or $R_1$ and $R_2$ together with the carbon atom to which they are attached form a carbocyclic ring of 3 to 8 atoms;

$R_3$ is hydrogen, $C_{1-3}$alkyl, halogen, $C_{1-3}$alkoxy, hydroxy or hydroxy$C_{1-3}$alkyl;

R is $CH_3CH_2OH$, $CO_2H$, or $CH_2OCR_4$ or

$R_4$ is $C_{1-3}$alkyl, phenyl or phenyl substituted with $R_3$;

$R_5$ is hydrogen or $C_{1-3}$alkyl or phenyl $C_{1-3}$alkyl or phenyl $C_{1-3}$alkyl in which the phenyl is substituted with $R_3$.

$R_6$ and $R_7$ are independently selected from hydrogen, $C_{1-3}$alkyl, phenyl or substituted phenyl in which the substituent is $R_3$.

m, n and p are independently 0 to 2; and a, b, c each represent single bonds or one of a, b, c represents a double bond or both a and c represent double bonds; and Z is hydrogen, $C_{1-5}$alkyl or $C_{1-5}$alkyl substituted with a member of the group consisting of phenyl, dimethylamino or acetylamino;

and pharmaceutically acceptable salts of the compounds of the formula (II) in which Z is hydrogen.

Except where specifically defined to the contrary, the terms alkyl, alkoxy and hydroxyalkyl include both the straight-chain and branched-chain species of the term. Halogen or halo is iodine, bromine, chlorine or fluorine.

One embodiment of this invention is the compounds of formulae (I) and (II) wherein the mercapto substituent is in a 2, 3 or 4-position to the pyridine ring, or the 2-position of the benzothiazole ring, and wherein formula (II) Z is hydrogen.

In one class of this embodiment

Q is

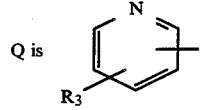

R is $CH_3$, $R_1$ is methyl and $R_2$ is methyl or hydrogen, and a, b, c are all single bonds or a and c are double bonds.

More specifically illustrating this class are the compounds wherein $R_3$ is hydrogen, $C_{1-3}$alkyl, halo or $C_{1-3}$alkoxy and m, n, and p are zero.

Exemplifying this class is the following compound:
6(R)-[2-8(S)-[2-methyl-2-(4-pyridinylthio)propionyloxyl-2(S),6(R)-dimethyl-1,2,6,7,8,8a(R)-hexahydronaphthyl-1-(S)]ethyl]-4(R)-hydroxy-3,4,5,6-tetrahydro-2H-pyran-2-one, and the corresponding ring opened dihydroxy acid.

In a second class, Q is

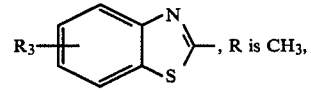, R is $CH_3$, $R_1$ is methyl and $R_2$ is methyl or hydrogen, and a, b, c are all single bonds or a and c are double bonds.

More specifically illustrating this class are the compounds wherein $R_3$ is hydrogen, $C_{1-3}$alkyl, halo or $C_{1-3}$alkoxy.

Exemplifying this class is the following compound:
6(R)-[2-[8(S)-[2-methyl-2-(2-benzothiazolyl)propionyloxy]-2(S),6(R)-dimethyl-1,2,6,7,8,8a(R)hexahydronaphthyl-2(S)]ethyl]]and the corresponding ring opened dihydroxy acid.

Another embodiment of this invention is the class of compounds of the formula (II) wherein Z is $C_{1-5}$alkyl and pharmaceutically acceptable salts of the compounds of formula (II) wherein Z is H.

The compounds of formula (I) wherein the 6-position of the polyhydronaphthyl ring contains a methyl group in the alpha configuration, are prepared by hydrolysis of the 8-acyloxy group of lovastatin followed by esterification of the resultant 8-hydroxy group with an appropriate acyl halide following the lithium bromide activated acylation procedure in copending U.S. application Ser. No. 038,580 filed Apr. 18, 1987. Alternatively the acylation can be accomplished following the standard acylation procedure in U.S. Pat. No. 4,444,784. The acyl halide can be prepared by reacting a mercaptopyridine, mercaptobenzothiazole or a substituted mercaptopyridine or substituted mercaptobenzothiazole in base with the appropriate 2-, 3- or 4-bromoester intermediate. The product ester of this reaction can be converted into an acyl halide by standard chemistry. Where the $R_3$ moiety contains a hydroxy group, that group can be protected using a silyloxy protecting group following the protection and deprotection procedures in U.S. Pat. No. 4,444,784.

2- and 4- mercaptopyridines are commercially available. 3-mercaptopyridines are described in *J. Am. Chem. Soc.*, 73, 1210 (1951).

Pyridinemethanethiols, wherein p=1, are known in the literature; a typical method of preparation is found in *Can. J. Chem.*, 56, 3060 (1978). Pyridineethanethiols, wherein p=2, are also known and described in *J. Het. Chem.*, 15, 1431 (1978).

2-Benzothiazolemethanethiols are prepared in *J. Chem. Soc.*, 916 (1955); 2-benzothiazoleethanethiols have been reported in a Russian publication CA, 61, 8288 (1964). Substituted mercaptopyridines and substituted benzothiazoles are known in the literature and/or could be prepared by standard organic reactions. If necessary, the mercaptan group can be protected and deprotected by using standard procedures as described in "Protective Groups in Organic Synthesis", T. W. Greene, J. Wiley & Sons N.Y., 1981, p. 195.

Oxidation of thio to sulfinyl or sulfonyl can be accomplished after acylation using standard mercapto oxidizing agents such as 3-chloroperbenzoic acid.

Compounds of formula (I) wherein R =CH$_2$OH or CO$_2$H or

or CO$_2$R$_5$ or

are prepared following the procedure detailed in copending U.S. patent application Ser. No. 048,136 filed May 15, 1987. An acyl halide formed from an appropriate mercaptopyridine or mercaptobenzothiazole is used in place of the acyl halides disclosed in the 048,136 reference.

Compounds of formula (I) wherein the 6-position contains a methyl group in the beta configuration are prepared from the corresponding 6-hydroxymethyl substituted analog following the procedure in copending U.S. patent application 092,354, filed Sept. 21, 1987. The 6-hydroxymethyl analog, in turn, is prepared following the procedure described in the above paragraph.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acid salts are basic amino acids, such as arginine, lysine, α,β-diaminobutyric acid or ornithine.

Preferred amines to form amine salts include t-octylamine, dibenzylamine, ethylenediamine, morpholine, and tri(hydroxymethyl)aminomethane. Also preferred is ammonia to form the ammonium salt.

Esters are preferably the alkyl esters, such as the methyl, ethyl, propyl, isopropyl, butyl, isobutyl or pentyl esters, of which the methyl ester is preferred. However, other esters such as phenylC$_{1-5}$alkyl, dimethylamino-C$_{1-5}$alkyl, or acetylamino-C$_{1-5}$alkyl may be employed if desired.

Metal salts of the carboxylic acids of formula (II) may be obtained by contacting a hydroxide, carbonate or similar reactive compound of the chosen metal in an aqueous solvent with the carboxylic acid of formula (II). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example a mineral acid (such as hydrochloric acid or sulphuric acid), a Lewis acid (for example boron trifluoride) or an acidic ion exchange resin. The solvent employed for this reaction is not critical, provided that it does not adversely affect the reaction; suitable solvents include the alcohol itself, benzene, chloroform, ethers and the like. Alternatively, the desired product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in *J. Med. Chem.*, 28, p. 347–358 (1985).

For estimation of relative inhibitory potencies, compactin (i.e., mevastatin) was assigned a value of 100 and the $IC_{50}$ value of the test compound was compared with that of compactin determined simultaneously in the published in vitro protocol.

Representative of the intrinsic HMG-CoA reductase inhibitory activities of the claimed compounds is the relative potency for 6R-[2-[8(S)[2-methyl-2-(4-pyridinylthio)propionyloxy]-2(S), 6(R)-dimethyl-1,2,6,7,8,8a(R)-hexahydronaphthyl-1(S)]ethyl]-4(R)-hydroxy-3,4,5,6-tetrahydro-2H-pyran-2-one of 112, and of 6(R)-[2-[8(S)-[2-methyl-2-(2-benzothiazolyl)propionyloxy]-2(S),6(R)-dimethyl1,2,6,7,8,8a(R)-hexahydronaphthyl-1(S)]ethyl]-4(R)-hydroxy-3,4,5,6-tetrahydro-2H-pyran-2-one as 100.

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100 mg) which may be given in two to four divided doses. Higher doses ma be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a non-toxic, therapeutically-effective amount of the compounds of formulae (I) or (II) or pharmaceutical compositions thereof.

The following examples illustrate the preparation of the compounds of the formulae (I) and (II) and their incorporation into pharmaceutical compositions and as such not to be considered as limiting the invention set forth in the claims appended hereto.

EXAMPLE 1

Preparation of 6(R)-[2-[8(S)-[2-methyl-2-(4-pyridinylthio)propionyloxy]-2(S),6(R)-dimethyl-1,2,6,7,8,8a(R)-hexahydronaphthyl-2( (a) Ethyl 2-methyl-2-(4-pyridinylthio)propionate 1 N NaOH (55 ml) was added to a solution of ethanol (100 ml) and water (100 ml). 4-Pyridinethiol (5.55 g, 0.05 mmol) was added to this mixture followed by the addition of ethyl 2-bromo-2-methylpropionate (8.1 ml, 0.055 mol). The mixture was stirred at room temperature overnight. The reaction mixture was then concentrated in vacuo and the residue partitioned between ether and water. The ether fraction was washed well with water, dried ($MgSO_4$), filtered and concentrated in vacuo to yield an oil which was shown by TLC (35% ethyl acetate/$CHCl_3$) and $^1H$ NMR to be the titled compound.

(b) 2-methyl-2-(4-pyridinylthio)propionic acid

A solution of 1.7 grams NaOH in 5 ml of water was added dropwise to a solution of 8.79 grams of ethyl 2-methyl-2-(4-pyridinylthio)propionate in 15 ml methanol. The solution was stirred at room temperature overnight, and then concentrated in vacuo to remove methanol. Concentrated HCl was added to the sodium salt and the mixture triturated with isopropanol and heated on the steam bath. The mixture was then cooled and filtered to remove sodium chloride. The filtrate was concentrated in vacuo and the resulting gummy solid dissolved by adding hot isopropanol. The mixture was cooled and filtered to give the title compound. The filtrate upon concentration and cooling gave a further yield of the title compound. M.P. 190°–192° C.; $^1$NMR and IR were both in agreement for the titled compound.

(c) 2-methyl-2-(4-pyridinylthio)propionyl chloride 9.7 g of the product from step (b) was refluxed for 2 1/2 hours in 225 ml thionyl chloride. The mixture was concentrated in vacuo. The residue was triturated and concentrated in vacuo two times with toluene to yield a white solid which showed the expected carbonyl shift in the IR, indicative of an acid chloride.

(d)
6(R)-[2-[8(S)-[2-methyl-2-(4-pyridinylthio]propionyloxy]-2(S),6(R)-dimethyl-1,2,6,7,8,8a(R)-hexahydronaphthyl-1(S)]ethy 1.0 grams of 6(R)-[2-[8(S)-hydroxy-2(S), 6(R)-dimethyl-1,2,6,7,8,8a(R)-hexahydronaphthyl-1(S)]-ethyl]-4(R)-tert-butyldimethylsilyloxy-3,4,5,6-tetrahydro-2H-pyran-2-one, and 163 mg of 4-pyrrolidinopyridine in 20 ml of pyridine were heated to 75° C. 2.3 grams of 2-methyl-2-(4-pyridinylthio)propionyl chloride from step (c) were added and the temperature maintained at 75° C. for about 13½ hours. The mixture was concentrated in vacuo and partitioned between ether/water. The ether layer was washed (5×50 ml $H_2O$) dried with $MgSO_4$ and filtered and concentrated to yield the title compound as an impure solid. The crude product was chromatographed on a 60 mm diameter column packed with 230–240 mesh silica gel under 10 lbs pressure and eluted with 3% methanol/chloroform. The major fraction was rechromatographed on a 40mm column with 1% methanol/chloroform as the developing solvent. The title compound was obtained and found by $^1$NMR and HPLC to be greater than 95% pure.

(e)
6(R)-[2-[8(S)-[2-methyl-2-(4-pyridinylthio)propionyloxy-2(S),6(R)-dimethyl-1,2,6,7,8,8a(R)hexahydronaphthyl-1(S)]ethyl]-

492 mg of the pure silyl ether from step (d) were dissolved in 5 ml dry THF. 0.2 ml of acetic acid was added followed by 2.4 ml of 1M tetra-n-butylammonium fluoride in tetrahydrofuran. The mixture was stirred at room temperature for 24 hours, concentrated in vacuo, and partitioned between ether and water. The ether solution was washed with saturated $NaHCO_3$ solution, and then diluted with 50 ml ethyl acetate. The aqueous extracts were extracted with ethyl acetate and all the organic mixtures combined, washed ($H_2$), satd $NaHCO_3$, brine) and then dried with $MgSO_4$, filtered and concentrated to yield the title compound as an impure solid. The impure solid was chromatographed on a 30 mm diameter 230–400 mesh silica gel column starting with 15% isopropanol/hexane and increasing polarity to 30% isopropanol/hexane. The appropriate fractions were then recrystallized from $CHCl_3$/hexane; filtered and collected to yield the titled compound as a solid with M.P. 158°–159° C.

Elemental Analysis Calc'd for: $C_{28}H_{37}NO_5S$ C 67.30, H 7.46, N 2.80, Found: 67.46, 7.46, 2.82

EXAMPLE 2

Preparation of 6(R)-[2-[8(S)-[2-methyl-2-(2-benzothiazolyl)propionyloxy]-2(S),6(R)-dimethyl1,2,6,7,8-,8a(R)-hexahydronaphthyl-1(S)]ethyl]-4(R)-hydroxy-3,4,5,6-tetrahydro-2H-pyron-2-one.

(a) ethyl 2-methyl-2-(2-benzothiazolyl)propionate 3.8 grams of sodium hydroxide was dissolved in 50 ml water. The solution was cooled and to this cooled solution was added 50 ml ethanol. 15 grams of 2-mercaptobenzothiazole was added and the solution diluted with 25 ml ethanol and 25 ml water. Following the addition of 17.5 grams of ethyl 2-bromoisobutyrate the mixture was stirred overnight. The reaction mixture was then concentrated in vacuo and the residue partitioned between ether and water. The ether fraction was washed, ($H_2O$ and aqueous $Na_2CO_3$) dried ($MgSO_4$), filtered and concentrated in vacuo. This mixture was then partitioned between ether and 10% sodium hydroxide. The ether fraction was washed with 2×25 ml 10% sodium hydroxide and then brine. The ether layer was then dried ($MgSO_4$), filtered, and concentrated to yield a solid which was shown by TLC ($CHCl_3$ and 3% isopropanol/hexane) and $^1H$ NMR to be the titled compound. (b) 2-methyl-2-(2-benzothiazolyl)propionic acid 14.48 grams of the ester from part(a) was dissolved in 30 ml $CH_3OH$. A solution of 2.26 g NaOH in 10 ml water was added dropwise. An oil formed and an additional 30 ml methanol and 10 ml water was added and stirring continued overnight. The solution was concentrated in vacuo. The residue was suspended in ether and to this mixture was added 30 ml 2N HCl. The mixture was diluted with more ether and the ether fraction washed with a small amount of water, then brine and then dried ($MgSO_4$), filtered and concentrated to yield a steely yellow solid which was recrystallized from isopropanol. The product solid had a M.P. 154°–155° C. TLC ($CHCl_3 R_f=0.1$, 20% isopropanol/hexane $R_f=0.75$)

Elemental Analysis Calc'd for: $C_{11}H_{11}NO_2S$ C 52.15, H 4.38, N 5.53 Found: C 52.03, H 4,54, N 5.85

(c) 2-methyl-2-(2-benzothiazolyl)propionyl chloride 3 grams of the acid from step (b) was combined with 10 ml thionyl chloride and 2 drops dimethyl formamide. The mixture was refluxed for 2 ½ hours, concentrated in vacuo and triturated 2X with hot toluene. The resulting mixture was concentrated in vacuo, and dried under high vacuum overnight to yield the titled compound as a solid of M.P. 228°–229° C.

(d)
6(R)-[2-[8(S)-[2-methyl-2-(2-benzothiazolyl)propionyloxy]-2(S),6(R)-dimethyl-1,2,6,7,8,8a(R)hexahydronaphthyl-1(S)]ethyl]-4(R)-tert-bytyldimethylsilyloxy-3,4,5,6tetrahydro-2H-pyran-2-one.

2.7 g of the acid chloride from part(c) was suspended in 50 ml pyridine, and to this was added 1.1 g lithium bromide. The mixture was heated at 50° C. for 1 hour. 4-Pyrrolidinopyridine (89 mg) was added and the mixture heated to 75° C. 1.1 g of 6(R)-[2-[8(S)-hydroxy-2(S),6(R)-dimethyl1,2,6,7,8,8a(R)-hexahydronaphthyl-1(S)]ethyl]-4(R)-tert-butyldimethylsilyl-oxy-3,4,5,6-tetrahydro-2H-pyran--2-one was added and the mixture heated at 75° C. for 15 hours. The resulting mixture was filtered and the filtrate concentrated in vacuo. The residue was partitioned between $H_2O$ and ether. The ether fraction was washed ($H_2$), saturated $NaHCO_3$ and brine), dried ($MgSO_4$), filtered, and concentrated to yield a gum which was chromatographed on a 50 mm diameter column with 230–400 mesh silica gel, using 15% ethyl acetate/hexane. A second chromatography employing a 40 mm column was necessary to achieve full purification. A solid product was isolated which was shown by NMR to be the title compound.

(e)
6(R)-[2-[8-(S)-[2-methyl-2-(2-benzothiazolyl)propionyloxy]-2(S),6(R)-dimethyl-1,2,6,7,8,8a(R)hexahydronaphthyl-1(S)]ethyl 340 mg of the product from step (d) was dissolved in 7 ml THF at room temperature and 0.12 ml HOAc was added followed by the addition of 1.53 ml of 1.0M tetra-n-butylammonium fluoride in tetrahydrofuran. The mixture was stirred overnight. After 26 hours the mixture was concentrated in vacuo. The residue was partitioned between ether and water and the ether fraction washed ($H_2O$, satd $NaHCO_3$, $H_2O$, 1N HCl, brine) dried ($MgSO_4$), filtered and concentrated in vacuo to yield a solid which was purified by silica gel chromatography with 12% isopropanol/hexane as a developing solvent. The chromatographed compound was recrystalized from ether/hexane to yield a crystalline solid of M.P. 135°–137° C. of 98.65 purity as shown by HPLC.

Elemental Analysis Calc'd for: $C_{30}H_{37}NO_5S_2$ C 64.83 H 6.71 N 2.52 Found: C 65.08 H 7.09 N 2.69

EXAMPLE 3

Preparation of Ammonium Salts of Compound II

The lactone (1.0 mmol) from Example 1 Step e is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried ($MgSO_4$). The $MgSO_4$ is removed by filtration and the filtrate saturated with ammonia (gas) to give the ammonium salt.

EXAMPLE 4

Preparation of Alkali and Alkaline Earth Salts of Compounds II

To a solution of 49 mg of lactone from Example 1 Step e in 2 ml of ethanol is added 1 ml of aqueous 0.1N NaOH. After one hour at room temperature, the mixture is taken to dryness in vacuo to yield the desired sodium salt.

In like manner, the potassium salt is prepared using one equivalent of potassium hydroxide, and the calcium salt, using one equivalent of CaO.

EXAMPLE 5

Preparation of Ethylenediamine Salts of Compounds II

To a solution of 0.50 g of the ammonium salt from Example 3 in 10 ml of methanol is added 0.04 ml of ethylenediamine. The methanol is stripped off under vacuum to obtain the desired ethylene diamine salt.

EXAMPLE 6

Preparation of Tris(hydroxymethyl)aminomethane Salts of Compounds II

To a solution of 202 mg of the ammonium salt from Example 3 in 5 ml of methanol is added a solution of 50 mg of tris(hydroxymethyl)aminomethane in 5 ml of methanol. The solvent is removed in vacuo to afford the desired tris(hydroxymethyl)aminomethane salt.

EXAMPLE 7

Preparation of L-Lysine Salts of Compounds II

A solution of 0.001 mole of L-lysine and 0.0011 mole of the ammonium salt from Example 3 in 15 ml of 85% ethanol is concentrated to dryness in vacuo to give the desired L-lysine salt.

Similarly prepared are the L-arginine, L-ornithine, and N-methylglucamine salts.

EXAMPLE 8

Preparation of Tetramethylammonium Salts of Compounds II

A mixture of 68 mg of ammonium salt from Example 3 in 2 ml of methylene chloride and 0.08 ml of 24% tetramethylammonium hydroxide in methanol is diluted with ether to yield the desired tetramethylammonium salt.

EXAMPLE 9

Preparation of Methyl Esters of Compounds II

To a solution of 400 mg of lactone from Example 1 Step e in 100 ml of absolute methanol is added 10 ml 0.1 M sodium methoxide in absolute methanol. This solution is allowed to stand at room temperature for one hour, then is diluted with water and extracted twice with ethyl acetate. The organic phase is separated, dried ($Na_2SO_4$), filtered and evaporated in vacuo to yield the desired methyl ester.

In like manner, by the use of equivalent amounts of the alkoxides derived from propanol, butanol, isobutanol, t-butanol, amyl alcohol, isoamyl alcohol, 2-dimethylaminoethanol, benzyl alcohol, phenethanol, 2-acetamidoethanol and the like, and employing the corresponding alcohol as solvent, the corresponding esters are obtained.

EXAMPLE 10

Preparation of Free Dihydroxy Acids

The sodium salt of the compound II from Example 4 is dissolved in 2 ml of ethanol-water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative derived slowly reverts to the corresponding parent lactone on standing at room temperature.

EXAMPLE 11

As a specific embodiment of a composition of this invention, 20 mg of lactone from Example 1 Step e is formulated with sufficient finely divided lactose to provide a total amount of 580 to 590 mg to fill a size 0, hard-gelatin capsule.

What is claimed is:

1. A compound represented by structural formulae (I) and (II):

wherein:

Q is [pyridyl structure with $R_3$] OR $R_3$-[benzothiazolyl structure]

R is $CH_3$, $CH_2OH$, $CO_2H$, or $CH_2OCR_4$ or $CO_2R_5$ or $$\underset{O}{\overset{\parallel}{C}}NR_6R_7;$$

$R_1$ and $R_2$ are independently hydrogen or $C_1$-alkyl or $R_1$ and $R_2$ together with the carbon atom to which they are attached form a carbocyclic ring of 3 to 8 atoms;

$R_3$ is hydrogen, $C_{1-3}$alkyl, halogen, $C_{1-3}$alkoxy, hydroxy, or hydroxy$C_{1-3}$alkyl;

$R_4$ is $C_{1-3}$alkyl, phenyl, or phenyl substituted with $R_3$;

$R_5$ is hydrogen, $C_{1-3}$alkyl, phenyl $C_{1-3}$alkyl or phenyl $C_{1-3}$alkyl in which the phenyl is substituted with $R_3$;

$R_6$ and $R_7$ are independently selected from hydrogen, $C_{1-3}$alkyl, phenyl or substituted phenyl in which the substituent is $R_3$;

m, n and p are independently 0 to 2; and a,b,c each represent single bonds or one of a, b, c represents a double bond or both a and c represent double bonds;

halogen is Br, Cl, F or I;

Z is hydrogen, $C_{1-5}$alkyl or $C_{1-5}$alkyl substituted with a member of the group consisting of phenyl, dimethylamino or acetylamino; and pharmaceutically acceptable salts of the compounds of the formula (II) in which Z is hydrogen.

2. A compound of claim 1, where Q is

Q is 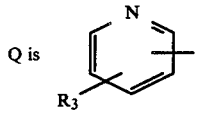

and R is methyl.

3. A compound of claim 2 wherein $R_1$ is methyl and $R_2$ is methyl or hydrogen, and a, b, c are all single bonds or a and c are double bonds.

4. A compound of claim 3 wherein $R_3$ is hydrogen, $C_{1-3}$alkyl, halo or $C_{1-3}$alkoxy.

5. A compound of claim 4 wherein $R_3$ is hydrogen, a and c are double bonds, and m, n and p are zero.

6. A compound of claim 5 which is: 6(R)-[2-[8(S)-[2-methyl-2-(4-pyridinylthio)propionyloxy]-2(S),6(R)-dimethyl-1,2,6,7,8,8a(R)-hexahydronaphthyl-1(S)]ethyl]-4and the corresponding ring opened dihydroxy acid.

7. A compound of claim 1, wherein

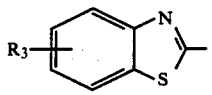

and R is methyl.

8. A compound of claim 7, wherein $R_1$ is methyl and $R_2$ is methyl or hydrogen, and a, b, c are all single bonds or a and c are double bonds.

9. A compound of claim 8 wherein $R_3$ is hydrogen, $C_{1-3}$alkyl, halo or $C_{1-3}$alkoxy.

10. A compound of claim 9 wherein $R_3$ is hydrogen, a and c are double bonds and m, n and p are zero.

11. A compound of claim 10 which is 6R-[2-[8(S)-[2-methyl-2-(2-benzothiazolyl)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyron-2-one; and the corresponding ring opened dihydroxy acid.

12. A hypocholesterolemic, hypolipidemic pharmaceutical composition comprising a pharmaceutically acceptable carrier and a nontoxic effective amount of a compound as defined in claim 1.

13. A composition of claim 12 in which the compound is selected from:
(a) 6(R)-[2-[8(S)-[2-methyl-2-(4-pyridinylthio)propionyloxy]-2(S),6(R)-dimethyl-1,2,6,7,8,8a(R)-hexahydronaphthyl-1(S)]ethyl ]-4(R)-hydroxy-3,4,5,6-tetrahydro-2H-pyron-2-one; and the corresponding ring opened dihydroxy acid;
(b) 6(R)-[2-[8ISO-[2-methyl-2-(2-benzothiazolyl)propionyloxy]-2(S),6(R)-dimethyl-1,2,6,7,8,8a(R)-hexahydronaphthyl-1 and the corresponding ring opened dihydroxy acid.

14. The method of inhibiting cholesterol biosynthesis comprising the administration to a subject in need of such treatment a nontoxic therapeutically effective amount of a compound of claim 1.

15. A method of claim 14 in which the compound is selected from:
(a) 6(R)-[2-[8(S)-[2-methyl-2-(4-pyridinylthio)propionyloxy]-2(S),6(R)-dimethyl-1,2,6,7,8,8a-(R)-hexahydronaphthyl-1-(S)]and the corresponding ring opened dihydroxy acid;
(b) 6(R)-[2-[8(S)-[2-methyl-2-(2-benzothiazolyl)propionyloxy]-2(S),6(R)-dimethyl-1,2,6,7,-8,8a(R)-hexahydronaphthyl-1(S)]ethyl]-4(R)-hydroxy3,4,5,6-tetrahydro-2H-pyran-2-one; and the corresponding ring opened dihydroxy acid.

* * * * *

UNITED STATES PATENT AND TRADEMARK OFFICE
CERTIFICATE OF CORRECTION

PATENT NO. : 4,866,068

DATED : September 12, 1989

INVENTOR(S) : C. S. Rooney

It is certified that error appears in the above-identified patent and that said Letters Patent is hereby corrected as shown below:

The structure at column 1, lines 40-45, should be:

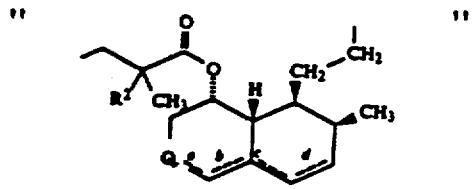

At column 3, lines 31-35, the definition of R should be:

"R is $CH_3$, $CH_2OH$, $CO_2H$, or $CH_2O\overset{O}{\underset{\|}{C}}R_4$ or $CO_2R_5$ or $\overset{O}{\underset{\|}{C}}NR_6R_7$;"

At column 4, lines 34-37, the name of the exemplified compound should be
"6(R)-[2-[8(S)-[2-methyl-2-(2-benzothiazolylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one";

UNITED STATES PATENT AND TRADEMARK OFFICE
CERTIFICATE OF CORRECTION

PATENT NO. : 4,866,068
DATED : September 12, 1989
INVENTOR(S) : C. S. Rooney

It is certified that error appears in the above-identified patent and that said Letters Patent is hereby corrected as shown below:

At column 7, lines 8-11, the name should be "6(R)-[2-[8(S)-[2-methyl-2-(4-pyridinylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one";

At column 7, lines 12-15, the name should be "6(R)-[2-[8(S)-[2-methyl-2-(2-benzothiazolylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one";

Column 7, line 27, should read "Higher doses may be favorably employed".

At column 7, lines 54-56, the name of the compound prepared through Example 1 should be: "6(R)-[2-[8(S)-[2-methyl-2-(4-pyridinylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one";

UNITED STATES PATENT AND TRADEMARK OFFICE
CERTIFICATE OF CORRECTION

PATENT NO. : 4,866,068
DATED : September 12, 1989
INVENTOR(S) : C. S. Rooney

It is certified that error appears in the above-identified patent and that said Letters Patent is hereby corrected as shown below:

At column 8, lines 28-30, the name of the compound under "d" should be:
"6(R)-[2-[8(S)-[2-methyl-2-(4-pyridinylthio) propionyloxy]-2(S),6(R)-dimethyl-1,2,6,7,8,8a(R)-hexahydronaphthyl-1(S)]ethyl]-4(R)-<u>tert</u>-butyl-dimethylsilyloxy-3,4,5,6-tetrahydro-2H-pyran-2-one";

At column 8, lines 52-55, the name of the compound under "e" should be:
"6(R)-[2-[8(S)-[2-methyl-2-(4-pyridinylthio) propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one";

At column 8, line 65, "($H_2$)" should be "($H_2O$,"

At column 9, lines 10-14, the name of the compound after "Preparation of" should be
"6(R)-[2-[8(S)-[2-methyl-2-(2-benzothiazolylthio) propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one";

UNITED STATES PATENT AND TRADEMARK OFFICE
CERTIFICATE OF CORRECTION

PATENT NO. : 4,866,068
DATED : September 12, 1989
INVENTOR(S) : C. S. Rooney

It is certified that error appears in the above-identified patent and that said Letters Patent is hereby corrected as shown below:

At column 9, line 16, the name after "(a)" should be "ethyl 2-methyl-2(2-benzothiazolylthio)propionate";

At column 9, line 34, the name "(b) 2-methyl-2-(2-benzothiazolylthio) propionic acid" should be set out as a separate line.

At column 9, line 52, the name after "(c)" should be "2-methyl-2-(2-benzothiazolylthio)propionyl chloride";

At column 9, lines 61-64, the name after "(d)" should be
"6(R)-[2-[8(S)-[2-methyl-2-(2-benzothiazolylthio)propionyloxy]-2(S),6(R)-dimethyl-1,2,6,7,8,8a(R)-hexahydronaphthyl-1(S)]ethyl]-4(R)-_tert_-butyldimethylsilyloxy-3,4,5,6-tetrahydro-2H-pyran-2-one".

At column 10, lines 19-21, the name after "(e)" should be
"6(R)-[2-[8(S)-[2-methyl-2-(2-benzothiazolylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one".

UNITED STATES PATENT AND TRADEMARK OFFICE
CERTIFICATE OF CORRECTION

PATENT NO. : 4,866,068
DATED : September 12, 1989
INVENTOR(S) : C. S. Rooney

It is certified that error appears in the above-identified patent and that said Letters Patent is hereby corrected as shown below:

In the Claims:

In Claim 1, column 12, lines 34-35, the definition of R should be:

"R is $CH_3$, $CH_2OH$, $CO_2H$, or $CH_2O\underset{\underset{O}{\|}}{C}R_4$ or $CO_2R_5$ or $\underset{\underset{O}{\|}}{C}NR_6R_7$".

In Claim 6, column 13, lines 16-20, after "which is", the name of the compound should be "6(R)-[2-[8(S)-[2-methyl-2-(4-pyridinylthio)propionyloxy]-2(S),6(R)-dimethyl-1,2,6,7,8,8a(R)- hexahydronaphthyl-1(S)]ethyl]-4(R)-hydroxy-3,4,5,6-tetrahydro-2H-pyran-2-one".

In Claim 11, lines 1-4, column 14, the name of the compound should be "6(R)-[2-[8(S)-[2-methyl-2-(2-benzothiazolylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one".

UNITED STATES PATENT AND TRADEMARK OFFICE
CERTIFICATE OF CORRECTION

PATENT NO. : 4,866,068
DATED : September 12, 1989
INVENTOR(S) : C. S. Rooney

It is certified that error appears in the above-identified patent and that said Letters Patent is hereby corrected as shown below:

In Claim 13, column 14, line 15, "pyron" should be "pyran".

In Claim 13, column 14, lines 17-20, the name after "(b)" should be
"6(R)-[2-[8(S)-[2-methyl-2-(2-benzothiazolylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one".

In Claim 15, column 14, lines 27-30, the name after "(b)" should be
"6(R)-[2-[8(S)-[2-methyl-2-(4-pyridinylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one".

UNITED STATES PATENT AND TRADEMARK OFFICE
CERTIFICATE OF CORRECTION

PATENT NO. : 4,866,068
DATED : September 12, 1989
INVENTOR(S) : C. S. Rooney

It is certified that error appears in the above-identified patent and that said Letters Patent is hereby corrected as shown below:

In Claim 15, column 14, lines 31-34, the name after "(b)" should be
"6(R)-[2-[8(S)-[2-methyl-2-(2-benzothiazolylthio)propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one".

Signed and Sealed this

Twenty-fifth Day of December, 1990

Attest:

HARRY F. MANBECK, JR.

*Attesting Officer*     *Commissioner of Patents and Trademarks*